United States Patent [19]

Berger

[11] 4,045,291
[45] Aug. 30, 1977

[54] TISSUE SPECIMEN CONTAINER

[76] Inventor: Jacob E. Berger, 4444 Main St., Snyder, N.Y. 14226

[21] Appl. No.: 705,416

[22] Filed: July 15, 1976

[51] Int. Cl.$^2$ .............................................. C12K 1/10
[52] U.S. Cl. .................................. 195/127; 206/818; 220/230
[58] Field of Search ............... 195/127, 139; 206/818; 220/230

[56] References Cited

U.S. PATENT DOCUMENTS

| | | | |
|---|---|---|---|
| 2,848,006 | 8/1958 | Simpson | 206/818 |
| 3,128,902 | 4/1964 | Barnum | 195/139 |
| 3,961,721 | 6/1976 | Gordon et al. | 206/818 |

*Primary Examiner*—Alvin E. Tanenholtz
*Attorney, Agent, or Firm*—Christel & Bean

[57] ABSTRACT

A tissue specimen container for pathological use consists of a hollow cylindrical body member which comprises a permanent magnet and ferro-magnetic end closures which are magnetically held against the end faces of the body member to complete the container. At least one of the end closures includes a screen portion for admitting treating fluid to the interior of the container.

7 Claims, 8 Drawing Figures

TISSUE SPECIMEN CONTAINER

BACKGROUND OF THE INVENTION

This invention relates to tissue specimen containers for use in the field of pathology.

In certain pathological procedures biopsy tissue specimens are subjected to microtomic slicing into thin layers for the preparation of slides for microscopic examination. Preliminary to the microtomy the tissue material is commonly subjected to a series of liquid treatment steps and for this purpose the tissue is placed in containers having surface portions of screen material to admit the treating fluid to the interior of the container.

Conventional containers for this purpose comprise a pair of relatively shallow cup-shaped members, one of which constitutes a cover which telescopes over the other member to close the same. Containers of this type are difficult to open and close and, since some of the tissue material is in the form of very small particles, escape of the material from closed containers of this type is not effectively prevented.

SUMMARY OF THE INVENTION

The present invention provides a tissue container and closure combination which seals the contents within the container in a highly effective manner and which is opened and closed with great facility. As in the prior art, the container of the present invention is of relatively flat cylindrical form. The body of the container consists of an annulus and the end walls are disposed against the opposed radial end walls of the annulus and are retained by magnetic force.

In a primary form the aforesaid annulus is of a permanent magnetic ceramic material and the end walls are of ferrous material and are retained securely against the end faces of the annulus by magnetic force. At least one of the end walls consists of an annulur steel member having a central portion of relatively fine screen material to admit treating fluid to the contents of the container when the latter is immersed in a bath of treating fluid but of a fineness to prevent escape of tissue material from the container.

In an alternative, the end members may be permanent magnets in which case the annular body element will be of magnetically attractable material. As a further alternative both the body member and one or both of the end members may comprise permanent magnets.

DESCRIPTION OF THE ILLUSTRATED EMBODIMENTS

Figure 1:
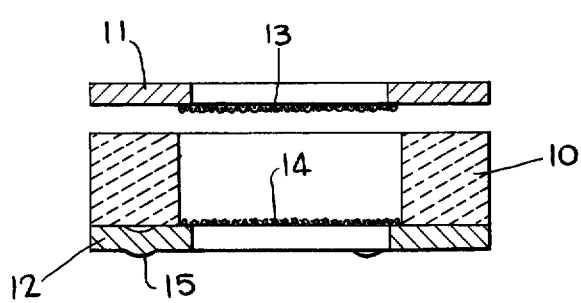
FIG. 1 is a cross-sectional view through one form of the tissue specimen container of the present invention.
Figure 4:
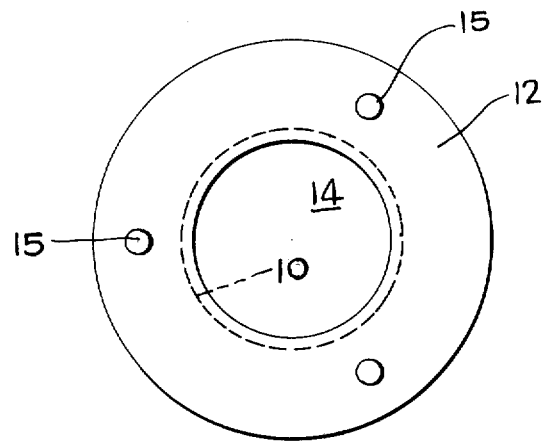
FIG. 4 is a bottom plan view of the embodiment of FIG. 1.

Referring first to the embodiment illustrated in FIGS. 1 and 4, the numeral 10 designates a main body member which consists of an annulus of magnetic ceramic material or other material providing a permanent magnet. In FIG. 1 the numerals 11 and 12 designate annular end plate members of steel or other material adapted to be magnetically attracted by the annulus 10. The internal diameters of the end members 11 and 12 are such as to provide ledges extending within the opening in body member 10 and screen discs are secured to these ledges as indicated at 13 and 14, respectively. The securement of screen members 13 and 14 to end memebers 11 and 12 may be welding, brazing, soldering, or by the use of any permanent adhesive material.

In this embodiment the outside diameters of the screen members 13 and 14 fit fairly snugly within the central opening in the body member 10 and thus serves to locate the end members 11 and 12 coaxially with respect to the body member 10. It will be seen that when end member 11 is applied to body member 10 in the same manner as illustrated in the case of end member 12, the several elements form a closed circular container excepting for the access provided by the relatively fine screen surfaces 13 and 14. If desired, only of the end surfaces need be provided with a screen surface, in which case one of the end members would comprise a solid disc.

In the embodiment illustrated in FIGS. 1 and 4 the end plate 12 is provided with circumferentially spaced bumps or protuberances 15. In depositing a number of the containers in a liquid bath of one kind or another it is convenient to stack the containers and the protuberances is space the several containers sufficiently to permit liquid access between the facing end members of adjacent containers.

Figure 2:
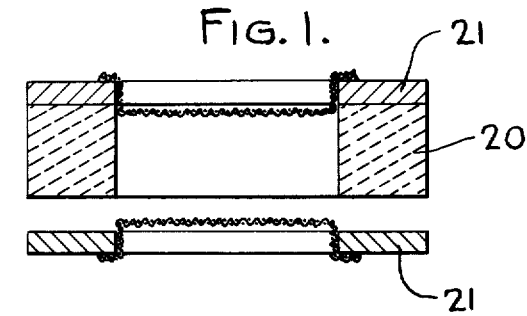
FIG. 2 is a similar view of another form of the container of the present invention.

In the embodiment of FIG. 2 a permanent magnet annulus 20 corresponding to the body member 10 of FIG. 1 is provided and in this embodiment the annular end plates, designated 21 and 22 are of the same inside and outside diameter as the body member 20. In this embodiment the screen members are of shallow cup-shape and have marginal flanges secured to the exterior surfaces of the end members 21. The screen members 22 are of slightly greater depth then the thickness of the end plates 121 and thus project slightly into the central opening of body member 20 and thus serve to locate the end members 21 concentrically with respect to body member 20.

It is to be understood that in the embodiment of FIG. 2 and in the other embodiments described later herein the protuberances designated 15 in FIGS. 1 and 4 may be employed for a like purpose and, if desired, only one surface of the end of a container need by provided with a screen surface, in which case, the opposite end member would be a solid disc as described above.

Figure 3:
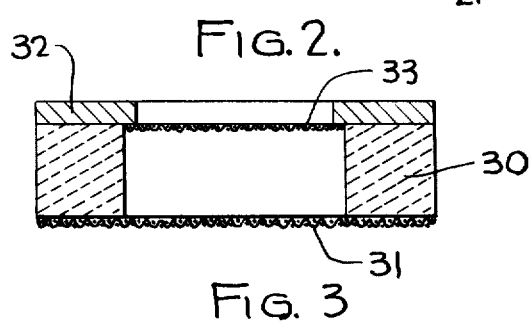
FIG. 3 is a similar view of a still further embodiment of the invention.

In the embodiment of FIG. 3 the body member 30 may be the same as the body members of the embodiments of FIGS. 1 and 2 and in this instance a screen surface is cemented, welded, brazed or otherwise permanently attached across one end face of body member 30 as shown at 31. In FIG. 3 an annular end plate 32 similar to the end plates of FIG. 1 is employed and in the illustrated instance a screen member 33 is permanently attached to the interior margin of annular end plate 32. In the embodiment of FIG. 3 the end plate structure 32, 33 may be as shown in FIG. 2 or in any of the other embodiments described later herein. Here again, if desired, the end plate 32, instead of being annular in form, may comprise a solid disc whereby liquid access to the interior of the container is solely by way of screen 31.

Figure 5:
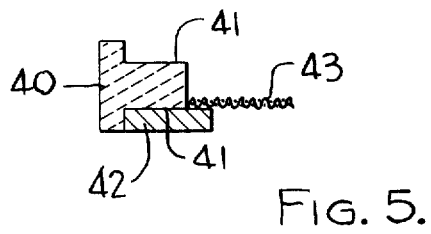

In the embodiments of FIGS. 5 through 8, for simplicity of illustration, only the left side of each of the annular body members is illustrated and, further the screened end construction at only one side of the body member is illustrated in the drawing. Referring to FIG. 5, an annular body member 40 is provided with annular recesses 41 at its opposite end faces and annular end plates or washers 42 seat within recesses 41 and are centered thereby. In FIG. 5 end plate 42 projects radially inwardly beyond the internal periphery of body member 40 and screen members 43 are attached to the inner margins of the end plates as described previously in connection with FIG. 1.

Figure 6:
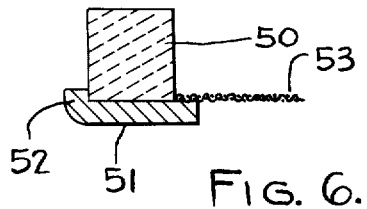

In the embodiment of FIG. 6 the annular body member is designated 50 and is of the same rectangular cross section as in the embodiments of FIGS. 1, 2 and 3. In this case, the annular end plates 51 have marginal flanges 52 which fit over the periphery of body member 50 to locate the plate members 51 concentrically with respect to body member 50. Here again, the plate members 51 project radially inwardly beyond the internal periphery of body member 50 and screem members 53 are attached to the inner margins of the end members 51.

Figure 7:
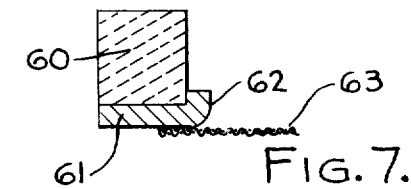
FIGS. 5, 6, 7 and 8 are fragmentary cross-sectional views through one side only of four further embodiments of the container of the present invention.

In the embodiment of FIG. 7 an annular body member 60 is likewise of rectangular cross-section and the annular end plates 61 have internal flanges 62 which fit within the central opening of body member 60 to locate the end plates 61 concentrically with respect to the body member 60. In this instance discoidal screen members 63 are attached to the exterior of each of the end plates 61.

Figure 8:
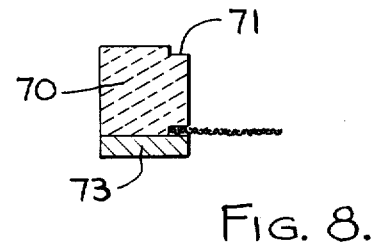

In the embodiment of FIG. 8 the annular body member 70 is provided with annular recesses 71 which receive discoidal screen members 72. In this instance, the end plates 73 may be of the same internal and external diameter as body member 70 and the screen members 72 are releasably held within recess 71 by end plates 73 and are not permanently attached to either the body member or the end members.

In any of the embodiments of FIGS. 5 through 8 one side of the body member may be closed by a solid disc so that a screen surface is provided at only one end face of the container. Also, protuberances similar to those designated 15 in FIGS. 1 and 4 may be provided in any of these embodiments for a like purpose.

The embodiments of FIG. 8 is merely illustrative and in this embodiment the body member 70 and one or both of the end members 73 may include centering formations such as are illustrated in the embodiments shown in FIGS. 5 and 6.

In a further alternative construction the screen material may be replaced by filter paper and in such case discs of filter paper may merely be held between the end washers and the end faces of the annular body member. Since some of the treating liquids employed in connection with processing of the tissue specimens are corrosive it is preferable to treat the steel surfaces by chrome plating, teflon coating or other non-corrosive surface treatment.

In a further variation of the present invention the end members may comprise permanent magnets in which case the annular body member may be of ferromagnetic material or may also comprise a permanent magnet.

If so desired, the marginal edge of either the body member or an end member may have a thumb-notch or similar recess to facilitate separation of the members.

Preferred embodiments of this invention having been hereinabove described and illustrated in the drawings, it is to be understood that numerous modifications thereof can be made without departing from the broad spirit and scope of this invention as defined in the appended claims.

While the various body members shown and described herein have been referred to as cylindrical, it is to be understood that such body members may be square or otherwise polygonal or of any other desired non-circular configuration

I claim:

1. A tissue specimen container comprising a tubular body member means and closure means adapted to extend across the opposite ends of said body member means in axial abutment therewith to form a tissue specimen receiving chamber, at least one of said means comprising permanent magnet means and the other of said means being magnetically attractable thereto whereby the container is releasably held in closed assembly by axially directed magnetic force.

2. A tissue specimen container according to claim 1 wherein said body member means comprises a permanent magnet and said end closure means is ferromagnetic.

3. A tissue specimen container according to claim 1 wherein said end closure means comprises a permanent magnet and said body member means is ferromagnetic.

4. A tissue specimen container according to claim 1 wherein the closure means at at least one end of said body member includes a screen portion for permitting fluid flow into and out of said chamber.

5. A tissue specimen container according to claim 4 wherein said screen portion fits within the opening in said tubular body member to center the closure means with respect to the body member.

6. A tissue specimen container according to claim 1 wherein said body member means and said closure means have interfitting portions for centering said means with respect to each other.

7. A tissue specimen container comprising a tubular body member, a screen secured across one end of said body member, and an end member at the opposite end of said body member in axial abutment with said body member, one of said members comprising a permanent magnet and the other of said members being magnetically attractable thereto whereby the end member at said opposite end is held against the body member by axially directed magnetic force.

* * * * *